United States Patent [19]

Morrison et al.

[11] Patent Number: 4,804,625
[45] Date of Patent: Feb. 14, 1989

[54] ASSAY PROCEDURES

[75] Inventors: Larry E. Morrison, Lisle; Garfield P. Royer, Warrenville, both of Ill.; Michael J. Heller, Poway, Calif.

[73] Assignee: Amoco Corporation, Chicago, Ill.

[21] Appl. No.: 656,011

[22] Filed: Sep. 27, 1984

[51] Int. Cl.⁴ .................. G01N 33/535; G01N 33/543; G01N 33/536

[52] U.S. Cl. ........................................... 435/7; 435/6; 435/810; 436/518; 436/536; 436/538; 436/805

[58] Field of Search ............... 436/512, 528, 536, 538, 436/542, 824, 541, 518, 805; 435/6, 7, 21, 28, 810

[56] References Cited

U.S. PATENT DOCUMENTS

| | | | |
|---|---|---|---|
| 4,231,999 | 11/1980 | Carlsson et al. | 435/7 |
| 4,268,663 | 5/1981 | Skold | 435/7 |
| 4,277,560 | 7/1981 | Gray et al. | 435/7 |
| 4,299,916 | 11/1981 | Litman et al. | 435/7 |
| 4,312,944 | 1/1982 | Mattiasson | 435/7 |
| 4,407,943 | 10/1983 | Cole et al. | 435/34 |
| 4,423,143 | 12/1983 | Rubenstein et al. | 435/7 |
| 4,530,900 | 7/1985 | Marshall | 435/7 |
| 4,576,912 | 3/1986 | Yaverbaum et al. | 435/7 |
| 4,587,212 | 5/1986 | Baker | 435/7 |
| 4,629,689 | 12/1986 | Diamond et al. | 435/7 |

Primary Examiner—Esther M. Kepplinger
Attorney, Agent, or Firm—Anthony J. Janiuk; William M. Magidson; Ralph C. Medhurst

[57] ABSTRACT

Binding assay methods involving determining the presence of analytes in samples through enzymatic formation of detectable substances in amounts related to the amount of analyte present in the sample and monitoring for the presence of the substances in distinct phases. Methods according to the invention include use of labelled materials which associate with the analyte to be determined or compete with the analyte for association with an added binder. The labelled materials employed include label portions which enzymatically form substances from substrates provided in or existing as a first phase, or, upon enzymatic treatment in a first phase, disassociate into substances capable of existing in or as a second distinct phase. Formation of the detectable substances is monitored by determining the transfer of the substance to a second distinct phase in contact with the first phase or by determining formation of a second distinct phase. The assays are useful in determining human IgG protein in blood samples and other constituents of blood or other biological samples without elaborate instrumentation, allowing for practice outside the clinical laboratory.

10 Claims, 4 Drawing Sheets

ASSAY PROCEDURES

BACKGROUND

The present invention relates generally to binding assays providing for determination of analytes in samples.

Assays directed to detection and quantification of physiologically significant materials in biological fluid and tissue samples are important tools in scientific research and in the health care field. Several different types of assay have been developed which are capable of detecting relatively highly concentrated components of common biological samples such as human serum. Such assays include high-resolution agarose gel electrophoresis and test procedures based on the catalytic activity of endogeneous enzymes. These methods generally do not have the sensitivity required to detect and quantify the numerous other physiologically important sample constituents which may be present at very low concentrations [e.g., endogeneous molecules intimately involved in cellular regulation (hormones, steroids, biochemical messengers); basic structural components of the organism (amino acids, proteins, polysaccharides); genetic material (DNA, RNA); vitamins, drugs and drug metabolites; toxins, pathogens and substances generated by the immune system].

The early biological assay techniques for the clinically important serum constituents such as the immunoprecipitation and immunodiffusion techniques developed in the 1940's also lacked the sensitivity necessary to detect and quantify most serum constituents of medical interest. In 1956 Berson and Yalow reported detection of soluble insulin-antibody complexes in the serum of insulin-treated diabetics injected with radiolabelled preparations of the serum hormone. See, Berson et al., *J. CLIN. INVEST.* 35: 170 (1956). The principles of this assay, commonly referred to as radioimmunoassay (RIA), were subsequently established and by the late 1960's the RIA was a major tool in endocrine laboratories. For example, virtually all the information now known about peptide hormonal physiology has resulted from the introduction of RIA and its ability to detect $10^{-10}$ to $10^{-12}$ molar concentrations of hormones.

The RIA assay technique was subsequently shown to be applicable to quantitative detection of any substance for which a specific antibody can be prepared, permitting development of a host of RIAs for chemical compounds such as drugs. In a broader sense the RIA principle has also been extended to systems in which other binding substances replace antibody, for example, in receptor assays. In 1980, the sales of immunodiagnostic reagents alone was estimated to be $229 million.

Although exhibiting the desired sensitivity, RIAs present several disadvantages inherent in the required reagents. The use of radioactive isotopes requires a special permit and a special laboratory. For this reason RIAs are performed by personnel separate from those in the routine clinical chemistry laboratory. Radiation can cause health hazards particularly for those working with the commonly used isotopes of iodine. In addition, the useful lifetime of the radiolabelled reagents employed is limited by half-life of the isotopes and the destructive processes that occur during isotopic decay. The equipment used to determine the amount of radioactivity in the samples is expensive and the counting of a series of samples is relatively time-consuming. (See, Smith et al., *AMER. CLIN. BIOCHEM.* 18: 253–74 (1981).) Overall, the amount of automation in the immunodiagnostic area is much less than that found in the routine clinical laboratory. Using an eight hour polyethylene glycol accelerated second antibody RIA for separation of free from bound antigen, only about 75–90 assays can be performed daily by a single technician employing manual pipettes and a single channel gamma counter.

To overcome the problems associated with RIA, immunoassay techniques employing nonisotopic labels have been developed. These nonisotopic assays, referred to as enzyme-linked immunoabsorbent assays (ELISA), fluoroimmunoassays (FIA), and luminescent immunoassay (LIA), according to the label employed, avoid many of the problems associated with RIAs and possess sensitivities near to that of the RIA. More recently, enzyme-linked assays have become increasingly popular and are replacing RIAs in many cases due to their more simple protocol relative to RIAs. As many as 2,000 assays per day can be run by a technician employing a solid-phase ELISA in microtiter plates with manual pipettes. These types of assays also have permitted the development of "homogeneous" immunoassays in which the bound and free labelled material need not be separated prior to the detection and measurement step. The RIA procedure requires the separation of free from bound labelled material for estimation of analyte concentration, a "heterogeneous" system. Sensitive assays in which antigen-antibody reactions could be detected without separation of free from complexed antigen are also more simple to automate.

Although superior to RIAs in several respects, the nonisotopic assays described above also exhibit problems caused by endogeneous interfering factors present in the reaction mixture. Proteins and other components commonly found in serum samples may exhibit fluorescent, chemiluminescent and enzymatic activity similar to that of the employed label. In addition, the activity of these labels may be inhibited by the presence of endogeneous compounds which absorb or scatter the emitted light of photophore-labels, similarly color compounds relative to chromophore labels, and catalytic enzymes which degrade enzyme labels. Determination of the activity of the employed label may also be impaired by the turbidity of the sample as in the case of whole blood samples. To a certain extent, these problems may be minimized by assay techniques employing a separation step wherein bound labelled material is separated from the sample, washed with buffer and the label activity is thereafter determined or wherein the separation of bound and unbound labelled material is achieved by partitioning them between immiscible aqueous phases. See, Mattiasson et al., *ADVANCES IN APPLIED MICROBIOLOGY* 28: 117–47 (1981); U.S. Pat. No. 4,312,944. However, the potential still exists that serum interfering components may be present. The determination step often requires use of photodetectors and other complex instrumentation generally available only in clinical laboratories.

There continues to exist in the art, therefore, a need for nonisotopic binding assays for determination of the presence of analytes which more rigorously avoid problems of interference inherent in detection and measurement steps of the assay and which avoid the need for sophisticated instrumentation while providing high sensitivity detection by methods which make them available for use in physicians' offices or elsewhere outside the clinical laboratory.

BRIEF SUMMARY

The present invention provides methods for the determination of analytes existing in a sample wherein the presence of analyte is determined by means of associating the analyte with an added labelled material, or by means of competition of the analyte with an added labelled material for association with an added binder for the analyte and labelled material. The improvements generally involve employing as part of the labelled material a label portion which catalyzes formation of a detectable substance from a substrate provided in or comprising a first phase; the detectable substance so formed being capable of existing in or comprising a second distinct phase. Alternatively, the label portion may serve as a substrate, which upon enzymatic treatment in an aqueous first phase, disassociates from the labelled material to form a detectable substance; the detectable substance so formed being capable of existing in or comprising a second distinct phase. Transfer of the substance to the second phase or formation of the second phase is determined and utilized to determine the presence of analyte in the sample. The association of the analyte with the labelled material or analyte and labelled material with added binder may involve any suitable form of covalent or noncovalent binding, e.g., antigen/antibody binding or nucleic acid hybridization.

In one presently preferred embodiment of the invention, an immunoassay for human immunoglobin IgG employs a human IgG labelled material having an alkaline phosphatase label portion which enzymatically converts hydrophilic p-phenylazophenyl phosphate substrate in an aqueous first phase into hydrophobic p-phenylazophenol detectable substance. The embodiment involves adding the labelled material and human IgG antibody to the sample, incubating the reaction mixture and separating the labelled material associated with antibody from the unassociated labelled material. Unassociated separated labelled material in the aqueous sample phase or separated associated labelled material disposed in an aqueous phase is contacted with the p-phenylazophenyl phosphate substrate under conditions allowing formation of p-phenylazophenol detectable substance. The aqueous first phase is contacted with a non-aqueous liquid second phase (an organic solvent), and the transfer of p-phenylazophenol to the organic liquid phase is determined by visual or colorometric means. Alternative embodiments may include use of other labelled materials such as a peroxidase labelled material which, in an aqueous phase and in the presence of air, catalyzes the conversion of methyloxobutanal substrate into butanedione detectable substance which possesses a relatively high vapor pressure and is detectable in a gaseous phase overlying the aqueous phase by olfactory means, phosphorescence or secondary reaction with other compounds. Other embodiments may employ collagenase labelled material which catalyzes the formation of soluble detectable substances which are capable of existing in a second distinct aqueous phase from solid collagen/blue dextran beads substrate disposed in the aqueous phase.

Binding assays according to the invention facilitate measurement of the detectable substance existing in or as a second distinct phase being either a liquid immiscible with the first phase or a distinct solid, liquid or gaseous phase relative to the first phase. Comprehended by the present invention are methods utilizing labelled materials having enzymes attached as part of the labelled portion which catalyze conversion of substrates provided in the first phase into substances which exist in distinct second phases. Also comprehended are methods wherein the label portion enzymatically forms or releases detectable substances which may exist in distinct second phases from a substrate which exists as a first phase. Examples of such labelled materials are labels comprising enzymes which catalyze formation of hydrophobic substances from hydrophilic substrates or the converse, the formation of solid, liquid or gaseous substances from solid or liquid substrates, the conversion of solid substrates soluble or insoluble in an aqueous phase into substances of opposite solubility characteristics and/or the release of substances from solid substrates. Also comprehended are methods wherein the labelled materials employed have labelled portions which, upon enzymatic treatment in a first phase, disassociate from the labelled materials and form detectable substances which exist in a second distinct phase or exist as the second distinct phase. Substances which may be formed and which are detectable by well-known means due to their inherent properties may be employed according to the invention and include compounds such as fluorophores, chromophores, chemiluminescent groups, enzymes, odoriferous compounds, and other compounds which may be selected due to their inherent properties which facilitate detection. The determination of detectable substances in distinct phases according to the improved assays of the present invention make them well suited for use in binary or "yes/no" type assays including home health care test kits and for use in industry for on-site tests for the presence of microorganisms, viruses, steroids, pesticides and antibodies.

As indicated above, the methods of the present invention provide analytical detection methods through enzymatically generating substances transferred in detectable quantities to or existing as distinct phases, in distinction to the methods disclosed by Mattiasson et al. wherein the bound labelled material ("conjugate") and unbound labelled material ("reactant") are asymmetrically partitioned in immiscible liquid phases and the label activity determined therein. See, Mattiasson et al., *ADVANCES IN APPLIED MICROBIOLOGY* 28: 117-47 (1982); U.S. Pat. No. 4,312,944.

Other aspects and advantages of the invention will become apparent upon consideration of the following detailed description wherein FIGS. 1 to 6 graphically illustrate improved binding assays for analytical determination of the presence of analytes in a sample through determining the presence of an enzymatically generated detectable substance existing in a distinct phase according to presently preferred embodiments of the invention.

DETAILED DESCRIPTION

Figure 1:
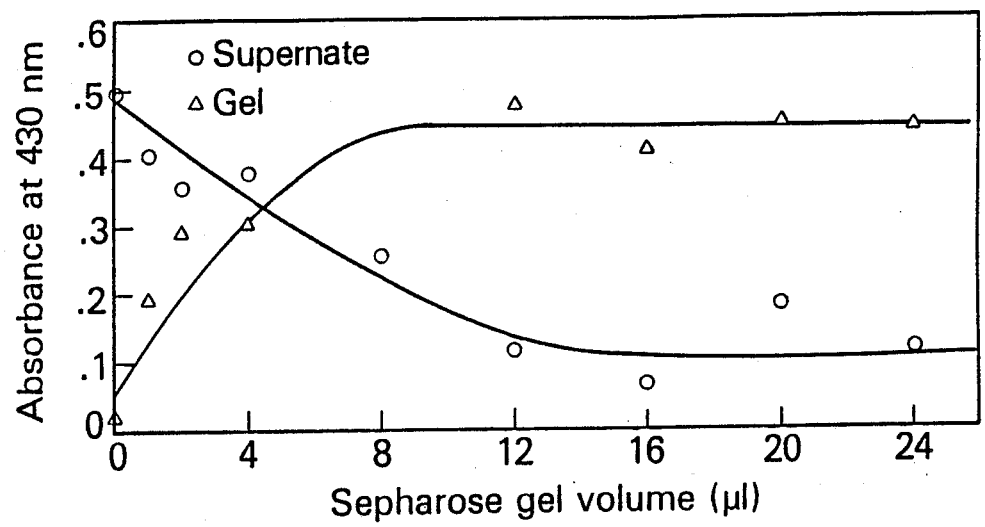

The following examples illustrate the practice of the invention according to certain preferred procedures. More specifically, they treat: preparation of exemplary labelled materials, i.e., alkaline phosphatase, peroxidase and collagenase conjugates of human immunoglobin IgG; the use of the alkaline phosphatase labelled materials to determine the presence of human immunoglobin IgG in aqueous serum samples; and the projected use of peroxidase and collagenase labelled materials in analytical assay procedures.

EXAMPLE 1

Preparation of Reagents for Human IgG Assay Using Detection of Detectable Substance in Distinct Phase

1. Materials

Human IgG (lot 19286), affinity purified (goat) anti-rabbit IgG (lot 15137) and (goat) anti-human IgG, $F_{ab}'$ fragment specific (lot 17026) were purchased from Cappel Laboratories (Malvern, Pa.). Succinimidyl 4-(N-maleimidomethyl)-cyclohexane-1-carboxylate (SMCC) and N-succinimidyl 3-(2-pyridyldithio) propionate (SPDP) were obtained from Pierce Chemical Company (Rockford, Illinois). Cyanogen bromide activated Sepharose 4B and the gel permeation media, Sephadex G-25 and Sephacryl S-200 and S-300, were obtained from Pharmacia Fine Chemicals (Piscataway, New Jersey). Alkaline phosphatase type VII-L (lot 72F-8110), collagenase (high purity, lot 33F-6819), pepsin (2×crystallized), peroxidase (type VI) dithiothreitol, mercaptoethylamine, Bis-tris, glutaraldehyde, gelatin, tris (hydroxymethyl) amino methane (Tris), 3-(cyclohexylamino) ethanesulfonic acid (Ches), glycine, 2-mercaptoethylamine, blue dextran, bovine serum albumin (fraction V) and the other proteins used for standardization of gel permeation columns, catalase, aldolase, chymotrypsinogen A, ovalbumin, and cytochrome c, were obtained from Sigma Chemical Company (St. Louis, Mo.). Inorganic buffers and other salts were reagent grade and obtained from either Fisher Scientific Company (Fiar Lawn, N.J.), Matheson Coleman and Bell (Norwood, Ohio), or Sigma Chemical Company. Toluene, spectrophotometric grad,e p-phenylazophenol, sodium, methanol, 2-butanone, methyl formate, and iodacetamide were obtained from Aldrich Chemical Company (Milwaukee, Wis.). Span 85 was obtained from Fluka. Other organic chemicals and solvents were reagent grade and obtained from either Aldrich Chemical Company or Fisher Scientific Company.

2. Chromatography Procedure

Gel permeation chromatography was performed in a refrigerated room at 4° C. Chromatography systems were purchased from Pharmacia Fine Chemicals and included peristaltic pumps (model P-1), glass columns fitted with flow adapters in one or both ends, sample applicators, and FRAC-100 or FRAC-300 fraction collectors. The absorbance of column effluents was continuously monitored with either Pharmacia UV-2 fixed wavelength absorbance monitors or a Gilson Medical Electronics, Inc. Holochrome variable wavelength monitor (Middleton, Wis.). In a typical chromatography experiment columns were flushed with about three column volumes of the buffer to be used for elution. Sucrose was added to the sample to a final concentration near 15% and sample added to the sample applicator. Column flow was initiated in the upflow direction and controlled by the peristaltic pump. The location of proteins in the fractions collected from the column was determined by the absorbance measurements made at 280 nm which were recorded using Pharmacia strip chart recorders.

3. Concentrations and Filtration Procedures

Concentration of proteins was performed using Amicon Corporation (Lexington, Mass.) Diaflo ultrafiltration membranes (PM10 or PM30) and Amicon concentration cells. Sterile filtration of samples was conducted using disposable syrings and Gelman Acrodisc disposable filter assemblies (Ann Arbor, Mich.) with 0.2 μm pore size.

4. Preparation of Alkaline Phosphatase-Antigen Conjugates

Alkaline phosphatase conjugate of human IgG was prepared by the reaction between a maleimide substituent on one protein and a sulfhydryl substituent on the other protein. Maleimide labelling of protein, using the heterobifunctional crosslinking agent, SMCC, and subsequent reaction with sulfhydryl labelled protein, was performed in a manner similar to that used by Yoshitake, et al., EUR. J. BIOCHEM. 101: 395–99 (1979). Incorporation of sulfydryl groups into proteins not possessing accessible sulfhydryl containing residues was accomplished using the heterobifunctional crosslinking reagent, SPDP, in procedures similar to those described by Carlsson, et al., *BIOCHEM. J.* 173: 723–37 (1978).

Alkaline phosphatase-human IgG ($F_{ab}'$ fragment) was prepared as follows. 20 mg of alkaline phosphatase was dissolved in 2 ml of 0.1M sodium phosphate at pH 7.0 and passed through a Sephadex G-25 column in the same buffer. The purified alkaline phosphatase was collected in 2.5 ml at the void volume. To this solution at 30° C. with stirring was added 112 μl of 8.92 mM SMCC in dioxane. The addition was made as nine separation additions of 12.5 μl each, separated by five minutes. Reaction was continued for a total time of about 100 minutes and then the solution was applied to a Sephadex G-25 column and eluted in 0.1M sodium phosphate, 1 mM EDTA, pH 7.0. Alkaline phosphatase labelled with maleimide groups was isolated at the void volume.

Human IgG (100 mg) was dissolved in 10 ml of water and dialyzed overnight in 1L of 0.1M sodium acetate/HCl, pH=4.3. Following dialysis, pepsin (3.0 mg) in 0.3 ml of the acetate buffer was added to the IgG solution and the solution sterile filtered into a sterile culture tube. This was then placed in a 37° C. water bath overnight. After 16 hours the solution was filtered and applied to a Sephacryl S-200 column (2.6 cm diameter, 100 cm length) and eluted in 0.1M sodium acetate/HCl at pH 5.0. The $(F_{ab}')_2$ fraction was isolated and concentrated to about 10 ml. The $(F_{ab}')_2$ concentration was determined by absorbance to be $5.47 \times 10^{-5}$M ($\epsilon_{280} = 1.22 \times 10^5$ M$^{-1}$ cm$^{-1}$). $5.7 \times 10^{-7}$ mole $(F_{ab}')_2$ was removed for use in the conjugate preparation while the remaining portion was stored in a refrigerator for later use. Sufficient dithiothreitol was dissolved in a small amount of the acetate buffer and added to the $(F_{ab}')_2$ solution such that the final concentration was equal to 0.015M dithiothreitol. This solution was then stirred for approximately 2 hours at 37° C. after which time it was applied to a Sephadex G-25 column and eluted in 0.1M sodium phosphate, 1 mM EDTA, pH 7.0. $F_{ab}'$ fragments containing sulfhydryl groups were recovered at the column void volume and immediately added to the previously prepared alkaline phosphatase labelled with maleimide groups. The combined solution wa then concentrated to about 7 ml, sterile filtered, placed in a sterile culture tube, and stirred at 4° C. overnight to allow conjugate formation. Following approximately 20 hours of reaction, 2-mercaptoethylamine was added to a final concentration of $5 \times 10^{-4}$M and allowed to react with unreacted maleimide groups at room temperature for about 3½ hours. The solution was then applied to the Sephacryl S-300 column and eluted in TBS. The product fractions were concentrated to about 2 ml and stored in a refrigerator.

5. preparation of Nonlabelled $F_{ab}'$ Fragments of Humans IgG.

$F_{ab}'$ fragments for use as unlabelled antigen were prepared from the $(F_{ab}')_2$ solution remaining from the procedure of paragraph 4, above. The solution was made 0.015M in dithiothreitol and stirred for about 2 hours at 37° C. The solution was then concentrated to about 2 ml and alkylation of sulfhydryl groups initiated by addition of iodoacetamide to a final concentration of 0.036M. This was allowed to react at room temperature for about 2 hours after which the solution was applied to the Sepharcryl S-300 column and eluted in TBS. The $F_{ab}'$ fraction, with sulfhydryl groups blocked by alkylation, was concentrated to about 2 ml and stored in a refrigerator.

6. Preparation of Alkaline Phosphatase Substrate.

The substrate chosen for the assay was p-phenylazophenyl phosphate. The phosphorylated dye was prepared according to the following procedure. To a solution of 1.98 g of p-phenylazophenol in 50 ml of tetrahydrofuran and 1 ml of pyridine was added 1 ml of phosphorous oxychloride ($POCl_3$). The reaction mixture was heated to reflux for a half hour and allowed to cool to room temperature. The mixture was then carefully poured into 100 ml of 2 N HCl solution and agitated thoroughly for 10 minutes at 60° C. to hydroyyze the acid chloride bonds. This procedure also allows the transfer of the free hydrogen phosphoric acid into the aqueous phase. Next, the organic phase was allowed to settle, the aqueous phase separated and discarded. The red organic layer was washed with 50 ml of 2 N HCl solution, and a red precipitate formed immediately. The precipitate was then filtered and washed with 2N HCl solution. The red precipitate was dissolved in 50% NaOH solution and adjusted to pH 10.3 by the addition of 2 N HCl solution. The basic aqueous solution was extracted with chloroform to remove the unreacted starting material until the chloroform extract became colorless. The desired free phosphoric acid was precipitated from the aqueous solution by adjusting the pH to 1.0. The product was then collected by suction filtration. The yield was 1.12 g (40%). 0.5 g of the p-phenylazophenyl-phosphoric acid was dissolved in 1 ml of concentrated ammonium hydroxide at room temperature. After one hour, the solvent was evaporated, yielding the corresponding ammonium salt quantitatively.

At pH 7.0 p-phenylazophenol is predominately in the neutral form which shows an absorbance maximum at 347 nm with an extinction coefficient equal to $2.0 \times 10^4$ $M^{-1} cm^{-1}$. These extinction coefficients assume 100% purity and anhydrous material, which may or may not be the case. An analysis of the p-phenylazophenyl phosphate indicates that 1.5 water molecules may be present. At pH 10.0 the phenolate anion predominates with absorbance maxima at 403 and 430 nm, each with extinction coefficients of $1.9 \times 10^4$ $M^{-1} cm^{-1}$. p-Phenylazophenyl phosphate was found to possess an absorbance spectrum which did not vary with pH. The absorbance maximum is at 340 nm with an extinction coefficient equal to $2.8 \times 10^4$ $M^{-1} cm^{-1}$. The absorbance spectrum of p-phenylazophenol was also recorded at pH 8.5. At this pH both the neutral and anionic phenol forms are present as evidenced by contributions of each to the absorbance spectrum. The concentration of each species was calculated from the extinction coefficients determined at pH 7.0 and pH 10.0. From these concentrations the acid dissociation constant of p-phenylazophenol was determined to equal to $2.7 \times 10^{-9} M^{-1}$ (pKa=8.6).

7. Preparation of Immobilized Antibodies.

(Goat) anti-human IgG, $F_{ab}'$ fragment specific antibodies were immobilized to cyanogen bromide activated Sepharose according to the procedure recommended by Pharmacia Fine Chemicals in their affinity chromatography manual. Two grams of activated Sepharose was swollen for 15 minutes in 20 ml of 1 mM HCl and then washed with 400 ml of the HCl solution. 35 mg of antibody was dissolved in 2.5 ml of 0.1M sodium bicarbonate at pH 8.3, applied to a Sephadex G-25 column, and eluted in the same buffer. The activated gel was then washed with 10 ml of the bicarbonate buffer and mixed immediately with the purified antibody collected at the void volume of the column. The gel/antibody mixture was then shaken with a slow rocking motion for 2 hours at room temperature after which time the supernate was removed and the gel washed alternately with large amounts of the bicarbonate buffer and 0.1M sodium acetate/HCl, 0.5M NaCl, pH 4.3 buffer. The gel was finally washed with TBS, the gel allowed to settle, and TBS added to provide a buffer/gel ratio equal to 1. The 1:1 gel:buffer solution was then stored in a refrigerator.

EXAMPLE 2

Immunoassay of Human IgG $F_{ab}'$ Fragments in Aqueous Buffer Based on Detection of Detectable Substance in a Distinct Liquid Phase 1. General Assay Procedures Assays of various concentrations of human IgG $F_{ab}'$ fragments dissolved in buffer were performed according to the following procedure. Alkaline phosphatase labelled antigen and the samples to be assayed were added to 1.5 ml capacity conical plastic tubes followed by addition of the gel containing immobilized antibodies. Gel was measured volumetrically from the 1:1 gel:buffer which was formed into a slurry by rapid stirring with a magnetic stir bar. For small gel volumes the 1:1 slurry was first diluted. The total solution volume was then brought to 0.6 ml with TBS containing 1% BSA, 1 mM $MgCl_2$, and 1mM $ZnCl_2$. The combined sample and reagent were rocked with an Ames (Elkhart, Ind.) Aliquot mixer for a period of time at room temperature, usually overnight for good equilibration. Supernate and gel were subsequently separated by centrifugation of the conical tubes in an Eppendorf (Brinkmann Instruments, Westbury, N.Y. Model 5414 centrifuge followed by removal of supernate with a Pasteur pipet. The gel was then washed several times by addition of TBS followed by mixing, centrifugation, and removal of the buffer. Supernate and gel fractoins were placed in separate disposable 13 mm×100 mm glass culture tubes with plastic screw caps to await initiation of the indicator reaction.

Three controls were run with each immunoassay series. In control I (C1) the assay tube contained gel and conjugate in the same amount as the other assay tubes in the series. In addition, a large excess of antigen was added, $10^{-6}$ mole. If the reagents are reacting properly, all conjugate should be found in the supernate of the sample. In control II (C2) the assay tube contained only the gel so that no enzyme activity should be found in supernate or gel phase. In control III (C3) only the conjugate was added so that maximum enzyme activity could be measured. The controls were equilibrated, phases separated, and the indicator reaction performed on each phase in a manner identical to that used for the other assay tubes in the series.

Indicator reaction was performed by adding TBS-BSA-metals (1% BSA, 1 mM $MgCl_2$, 1 mM $ZnCl_2$) buffer to each culture tube containing either supernate or gel, to a final volume of 1.2 ml. 1.5 ml of tuluene was added to each tube and the reaction initiated with addition of 200 μl of $5 \times 10^{-3}$M p-phenylazophenyl phosphate in TBS. The tubes were then gently rocked at room temperature and removed periodically for visual inspection and measurement of the absorbance of the toluene phase. For absorbance measurements the tubes were placed in a Spectronic 21 absorbance spectrometer (Bausch and Lomb, Rochester, N.Y.). The volume of the aqueous phase (1.4 ml) and toluene phase (1.5 ml) in the culture tubes allowed the light beam in the Spectrometer to pass only through the toluene phase so that only dye which partitioned into the toluene phase was measured.

2. Immunoassay of Human IgG $F_{ab}'$ Fragments in Buffer by Detection of p-Phenylazophenol in a Distinct Phase.

Figure 2:
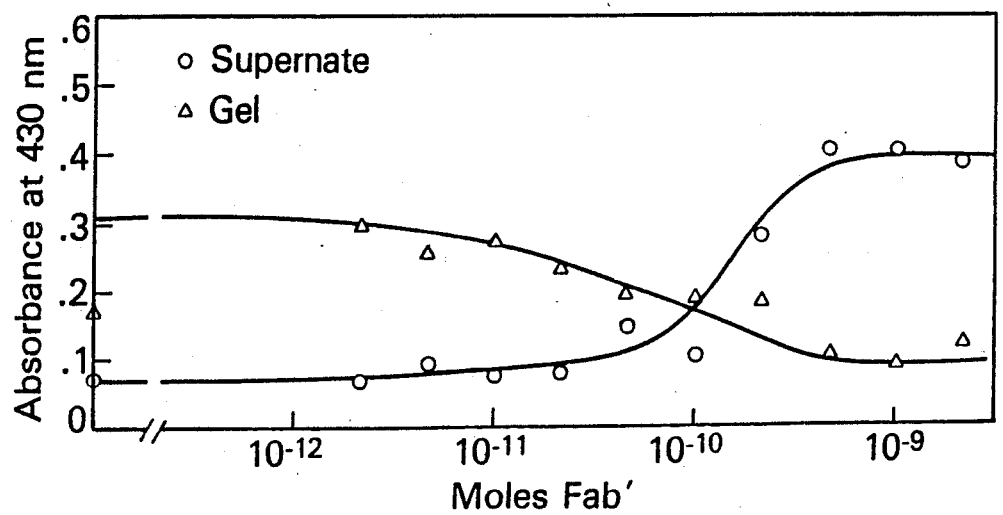

As a starting point for performing the assay, antibodies immobilized to Sepharose gel were titrated into alkaline phosphatase-antigen conjugate to determine the minimal amount of gel required to bind all the conjugate. Antibodies immobilized to the gel were (goat) anti-human IgG, $F_{ab}'$ fragment specific. Both supernate and gel were analyzed with the dye partitioning indicator reaction following equilibration of $10^{-11}$ mole conjugate with various amounts of gel. The dye absorbance in the toluene layer of supernates decreased as more gel was used, while the absorbance of the toluene layer of the gel samples increased. This indicates the binding of conjugate to antibodies immobilized on the gel. The data from this analysis is graphically illustrated in FIG. 1. From FIG. 1 it is apparent that 12 μl of gel is sufficient to remove all alkaline phosphatase activity from the supernate. The gel contained $3.3 \times 10^{-8}$ mole of antibody, at most, per ml of gel, since 5 mg of antibody was reacted per ml gel during the immobilization procedure. 12 μl of gel therefore contains $4 \times 10^{-10}$ mole of antibody which is, at most, a 40 fold excess over labelled antigen present in each sample. The concentration of conjugate is based upon an assumed 2:1 proportion of alkaline phosphatase to $F_{ab}'$ in the conjugate (fraction II) and a corresponding summation of extinction coefficients for the absorbance at 280 nm ($\epsilon_{280nm}$, alkaline phosphatase=$7.4 \times 10^4$ $M^{-1}$, $cm^{-1}$, $\epsilon_{280}$ nm, $F_{ab}'=2.1 \times 10^5$ $M^{-1}cm^{-1}$, there $\epsilon_{280nm}$, alkaline phosphatase-$F_{ab}'=2.1 \times 10^5$ $M^{-1}cm^{-1}$). The conjugate composition was inferred from the elution volume of the fractions recovered during the Sephacryl chromatography purification procedure. The assay was tested using $10^{-11}$ mole of the alkaline phosphatase -$F_{ab}'$ conjugate and 12 μl of gel per sample. Various solutions of human IgG $F_{ab}'$ fragments in TBS buffer were assayed according to the above-stated procedures and a typical series of results are presented in FIG. 2, following two hours of developing the indicator reaction. The supernate fractions from the samples generally showed fairly sharp transition in the amount of dye transferred to the toluene phase versus $F_{ab}'$ concentration. The gel fractions generally showed a more gradual transition. Supernate data may therefore be better used for "yes/no" type assays which are well suited to visual analysis, whereas gel data may be better suited to measuring antigen concentration, over a ten or hundred fold concentration range, using absorbance measurements. In the assay presented in FIG. 2, the transition from negative to positive indicator reactions occurs between $1 \times 10^{-10}$ and $2 \times 10^{-10}$ mole of $F_{ab}'$ ($7.1 \times 10^{-8}$ and $1.4 \times 10^{-7}$ M $F_{ab}'$) for the supernate fractions. Absorbance changes gradually between about $10^{-11}$ mole $F_{ab}'$ and $5 \times 10^{-10}$ mole $F_{ab}'$ ($7.1 \times 10^{-9}$ and $3.6 \times 10^{-7}$ M $F_{ab}'$) for the gel fractions.

EXAMPLE 3

Figure 3:
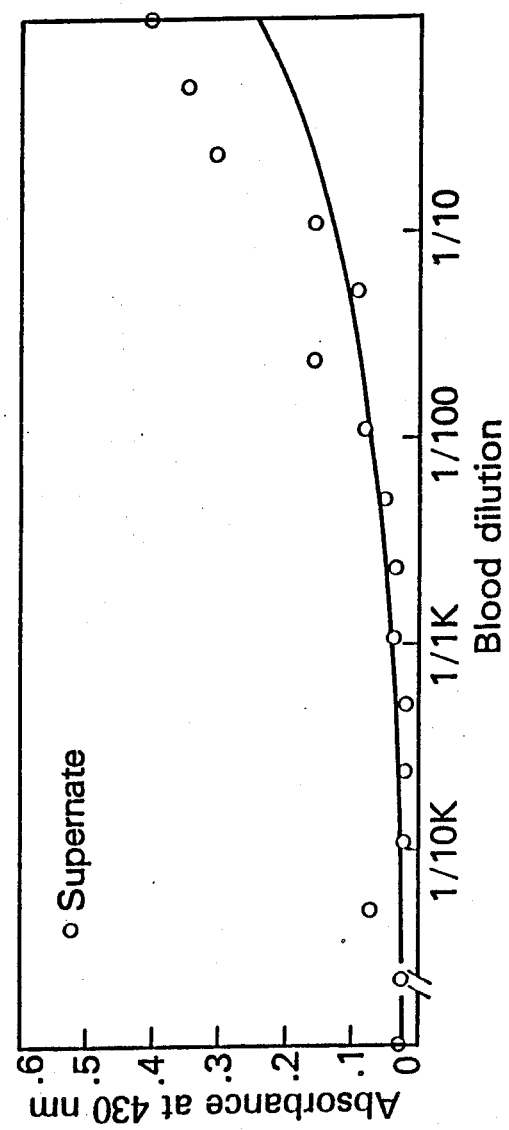

Immunoassay For Human IgG in Whole Blood Based on Detection of Detectable Substance in a Distinct Liquid Phase The human IgG $F_{ab}'$ fragment-alkaline phosphatase labelled material and anti-$F_{ab}'$ immobolized antibodies of Examples 1 and 2 were used to analyze for IgG in whole human blood according to the assay procedure of Example 2. Before performing the immunoassays, the blood was first examined for two possible soruces of interference. The first type of interference would be from any colored components in blood which are able to partition into toluene. To test for this, binary dilutions of whole blood in TBS were prepared, ranging from undiluted blood to blood diluted one part in 256, and mixed with toluene as would be performed in the assay. After 2 hours of mixing, no color was found in the toluene phase. The second type of interference would be from alkaline phosphatase which is known to be present in blood. Blood dilutions were again prepared and analyzed using the dye partitioning indicator reaction by adding p-phenylazophenyl phosphate and partioning this against toluene. The absorbance of the toluene phase was examined after two hours and the values plotted against each dilution are shown in FIG. 3. Absorbance values seen at dilutions less than 1 in 10 may be greater than the dye absorbance due to blood components sticking to the walls of the culture tubes and emulsion formation which results in higher absorbance values due to light scattering. Assay tubes containing the 8 most concentrated blood samples were examined after 2 hours. Some yellow color was visible in the three most concentrated solutions. The results indicate that assays performed upon blood dilutions of greater than 1 in 10 should be free of interference from native alkaline phosphatase activity.

Figure 4:
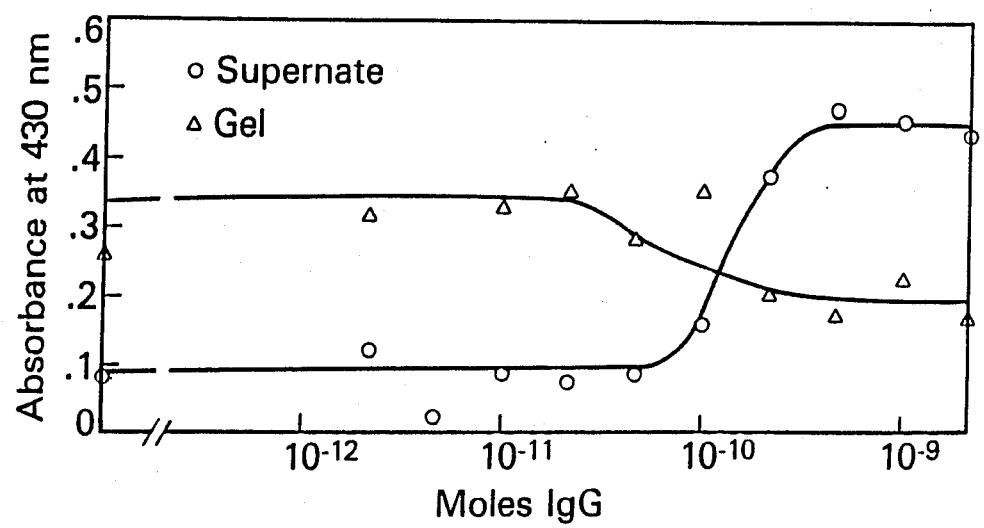
Figure 5:
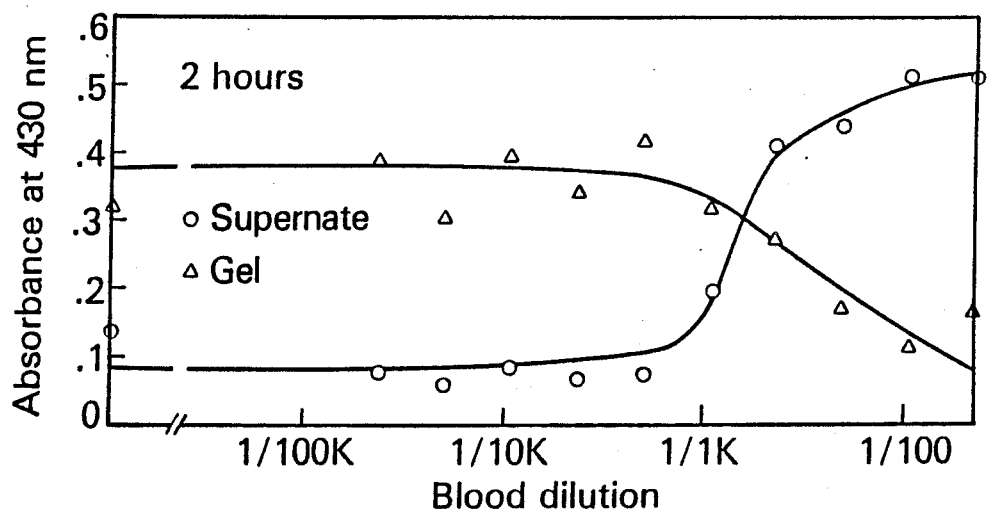
Figure 6:
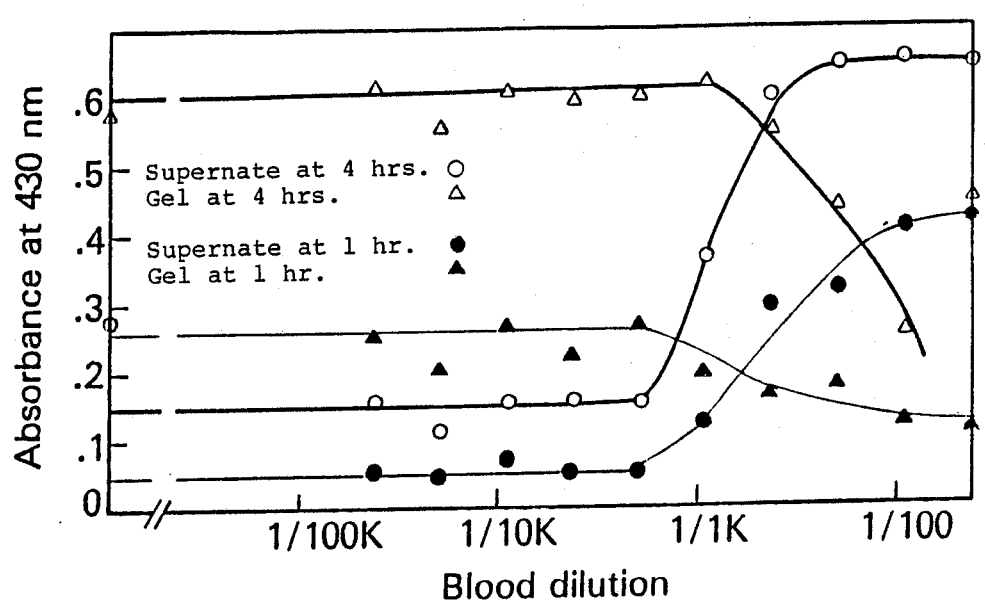

A calibration curve was prepared using binary dilutions of human IgG in TBS. Assays according to the procedures of Example 2 were performed on each dilution of antigen and the results are plotted in FIG. 4 for a development time of 2 hours. A transition in toluene absorbance is clearly seen in the supernate fractions between $1 \times 10^{-10}$ and $2 \times 10^{-10}$ mole human IgG ($7.1 \times 10^{-8}$M and $1.4 \times 10^{-7}$ M IgG). Immunoassays of blood dilutions were then performed. The results are presented in FIG. 5 for a 2 hour development time when the supernate coloration is clearly visible. Also presented in FIG. 6 is the data for immunoassays of whole blood at development times of 1 hour and 4 hours. The transition is clearly apparent at 1 hour and contrast continues to develop as development time is increased to 4 hours. Strong yellow coloration of the toluene layer in the positive supernate fractions was apparent and the aqueous layers have become colorless with formation of a white precipitate. The white precipitate results from the inorganic phosphate formed by dye hydrolysis. The phosphate precipitates with divalent metals present in the buffer. Since the gel fractions display more gradual change in toluene absorbance across the antigen concentration range, no transition in the supernate fractions can be visualized.

From the position of the transition in the supernate fractions of the blood dilutions and the IgG calibration curve, the concentration of IgG in the original blood sample may be calculated. The concentration of IgG in a normal adult is reported to be between 8 and 15 mg IgG/ml blood. Eastham, *BIOCHEMICAL VALUES IN CLINICAL MEDICARE* (John Wright & Sons 1978) p. 189. The concentration of IgG in the blood sample we tested was determined to be between 10 and 40 mg IgG/ml blood. The value overlaps with the normal IgG concentration range, as would be expected. The level of uncertainty in the assay result is a function of separation between concentrations of standard and sample which were assayed. The uncertainty in the concentration may be reduced by testing more dilutions of the blood sample and testing more concentrations of IgG in the calibration series.

EXAMPLE 4

Immunoassay Based on Detection of Detectable Substance in a Distinct Vapor Phase The following procedures are expected to be useful in practice of the invention.

1. Preparation of Peroxidase Labelled Antibody or Immunoglobulin Antigen.

Peroxidase-antibody conjugates were prepared by either of two procedures. In the first procedure, peroxidase is reacted with SMCC followed by reaction with $F_{ab'}$ particles of the antibody, as described in Example 1 for the preparation of alkaline phosphatase labelled human IgG $F_{ab'}$ particles. Table I shows the relative amounts of reagents used in each of three conjugations, and the composition of the conjugate obtained. Conjugate composition was determined by the absorbance spectrum assuming $\epsilon_{280}$ nm, $F_{ab'}$ particles $= 6.1 \times 10^4 M^{-1}$ and $\epsilon_{403 nm}$, peroxidase $= 1 \times 10^5 M^{-1}$. Correction was made for the absorbance of peroxidase at 280 nm.

TABLE I

| mole SMCC added per mole Peroxidase | mole peroxidase-SMCC added per mole $F_{ab'}$ | mole peroxidase conjugated per mole $F_{ab'}$ |
| --- | --- | --- |
| 50 | 5.4 | 2.0 |
| 49 | 5.1 | 1.7 |
| 50 | 5.0 | 0.82 |

In the second procedure to prepare peroxidase labelled antibodies, peroxidase and whole IgG antibodies were each reacted with SPDP separately. SPDP labelled peroxidase or antibody was then reacted with dithiothreitol to produce thiol labelled peroxidase or antibody which was then allowed to couple with the SPDP labelled antibody or peroxidase. This procedure is similar to that described by J. Carlsson, H. Drevin, and R. Axen, BIOCHEM. J., 173, 723-737 (1978). The following detailed description is typical. 12.6 mg of (Goat) anti-rabbit IgG in 2 ml of PBS was combined with 23.5 μl of 20 mM SPDP in ethanol. The solution was stirred gently at room temperature for one hour and then purified on a Sephadex G-25 column, eluted with 0.1M sodium acetate buffer at pH 4.5, containing 0.1N NaCl. Dithiothreitol was added to this solution in sufficient quantity to produce a 25 mM solution. This mixture was stirred for approximately 15 minutes at room temperature before concentrating and purifying on a Sephadex G-25 column eluted with 0.1N sodium phosphate at pH 7.5. Peroxidase (43 mg) was dissolved in 4 ml of 0.1N sodium phosphate at pH 7.5 containing 0.1N NaCl. To this was added 675uL of 20 mM SPDP and the resulting solution stirred for about 1 hour at which time the solution was applied to a Sephadex G-25 column and eluted with 0.1N sodium phosphate, pH 7.5. The derivatized peroxidase was obtained in the column void volume and concentrated to 2 ml. The peroxidase-SPDP was then combined with the derivatized antibody. This solution was concentrated to a total volume of 8 ml and allowed to react at room temperature, with stirring, for about 20 hours. The conjugate was isolated on a Sephadex G-100 column eluted with PBS.

The composition of the peroxidase-antibody conjugate prepared by the above procedure is listed as the first entry in Table II. Other conjugates prepared by similar procedures are also listed. While antibodies concentration was based upon an $\epsilon_{280}$ nm, $IgG = 2 \times 10^5 M^{-1}$.

TABLE II

| mole SPDP added per mole peroxidase | mole SPDP added per mole antibody | mole peroxidase added per mole antibody | mole peroxidase conjugated per mole antibody |
| --- | --- | --- | --- |
| 15 | 5.2 | 10 | 0.78 |
| 20 | 2.5 | 2.1 | 1.9 |
| 15 | 5.2 | 10 | 0.85 |

2. Synthesis of Peroxidase Substrate

The chosen peroxidase substrate, 2-methyl-3-oxobutanol (MOB) was prepared according to the general procedure of Diels, et al., Ber. Vol. 49, 158 (1916). 11.5 g sodium metal was combined with 25 ml methanol in 500 ml of anhydrous ether and allowed to stir overnight under nitrogen. The ether solution was then cooled in ice and 30.8 ml of methyl formate added followed by slow addition (½-1hr.) of 44.8 ml of 2-butanone. This was allowed to stir overnight at room temperature resulting in production of a slurry of white solid in a yellow solution. The solid was isolated by filtration and dissolved in 500 ml of ice water. To this was slowly added 150 ml of a chilled solution of 30 ml sulfuric acid in 300 ml of water. The acidified solution was then extracted with four portions of ether, 100 ml per portion. The combined ether fractions were then washed with 50 ml of water followed by washing with 2×50 ml portions of water containing saturated sodium chloride. The ether solution was dried with magnesium sulfate, filtered, and the ether removed by distillation. The solid product was purified by sublimation and stored at -80° C. The MOB was purified by a second sublimation prior to use.

3. Reaction of MOB with Oxygen and Peroxidase 2-methyl-3-oxobutanol (MOB) was found to react with dissolved oxygen in buffer solutions to produce 2,3-butanedione (biacetyl). This reaction is catalyzed by the enzyme peroxidase. The reaction course can be followed by chemiluminescent emission which accompanies the production of the biacetyl, or by oxygen consumption. Some data pertaining to the rate of reaction is presented in Table III. Oxygen consumption was measured with a Clark electrode and oxygen monitor (Yellow Springs Instrument Co., Inc., Yellow Springs, OH). Since one mole of biacetyl should be produced for each mole of oxygen consumed, 50% oxygen consumption corresponds to production of about $1.2 \times 10^{-4}$ M biacetyl in an air saturated solution. Note that addition of acetylacetone to the reaction mixture assisted oxygen uptake. Solutions tested were initially air saturated.

TABLE III

| [MOB] | [Peroxidase] | [Acetylacetone] | buffer | Time to production of $1.2 \times 10^{-4}$ M biacetyl (50% oxygen consumption) |
|---|---|---|---|---|
| $10^{-2}$ M | $10^{-7}$ M | 0 | 0.01 M BIS-TRIS, pH 6.5 | 6.5 sec |
| $10^{-3}$ M | $10^{-7}$ M | 0 | 0.01 M BIS-TRIS, pH 6.5 | 31 sec |
| $3 \times 10^{-4}$ M | $10^{-7}$ M | 0 | 0.01 M BIS-TRIS, pH 6.5 | 202 sec |
| $5 \times 10^{-3}$ M | $10^{-8}$ M | 0.01 M | 0.01 M TRIS, pH 7.5 | 12 sec |
| $10^{-3}$ M | $10^{-8}$ M | 0.01 M | 0.01 M TRIS, pH 7.5 | 32 sec |

The production of biacetyl in reactions of the type presented in Table III was confirmed by smell.

4. Immunoassay Procedure Using Detectable Substance in Distinct Vapor Phase.

Immunoassays using materials of sections 1 and 2 above may be performed according to any of several formats including the competitive format described in Examples 2 and 3 and "sandwich" type assay formats. The following is a description of a competitive assay format for goat IgG. Sample containing goat IgG is added to assay tubes containing anti-goat IgG immobilized to sepharose gel. To this mixture is also added peroxidase labelled goat IgG in an amount small enough to be completely bound by the immobilized antibody in the absence of sample antigen. This is equilibrated to allow competitive binding of sample antigen and peroxidase labelled antigen to the immobilized antibodies. Solid support and supernatant are then separated by filtration or centrifugation and either fraction analyzed by addition of sufficient MOB in 0.01M bis-tris, pH 6.5 to effect a final MOB concentration of $10^{-3}$M. Reaction is allowed to proceed for several minutes or longer in a capped tube. Presence of antigen in the sample is indicated by the presence of biacetyl in the vapor phase above the solution when the supernatant fraction is analyzed. When analyzing the gel fraction, the opposite is true. Biacetyl is a phosphorescent compound which may be measured by its vapor phase phosphorescence. Much more simply, however, biacetyl presence may be determined by its aroma. [Biacetyl is the major odoriferous component of butter and is detectable in aqueous solutions by its aroma at 2.3 parts per million ($2.7 \times 10^{-5}$M). (W.H. Stahl (ed.), *COMPILATION OF ODOR AND TASTE THRESHOLD VALUES DATA*, American Society for Testing and Materials, ASTM Data Series DS48, Philadelphia, PA.)] The data in Table III indicates that biacetyl is produced in amounts easily detectable by its aroma within minutes when $10^{-8}$ M peroxidase is present in solutions containing $10^{-3}$ M MOB. Acetylacetone may be added to facilitate the reaction.

EXAMPLE 5

Immunoassay Based on Detection of Solubilized Detectable Substance

The following procedures are expected to be useful in practice of the invention.

1. Preparation of Collagenase Labelled Material.

Collagenase-human $F_{ab}'$ conjugate was prepared by the same procedure described in Example 1 to produce alkaline phosphatase-human $F_{ab}'$ conjugate. 24 mg of high purity collagenase (1600u/mg protein) in 2.5 ml of 0.1N sodium phosphate buffer, pH 7.0 was reacted with 171 μl of 8.9 mM SMCC solution in dioxane. This was added in nine separate additions of 19 μl each, each addition separated by five minutes, while the protein solution was stirred in a 30° C. water bath. The reaction was allowed to continue for about one hour after all additions were made and then the derivatized collagenase was isolated in a Sephadex G-25 column eluted with 0.1N sodium phosphate, pH 7.0, containing 1 mM EDTA. A $(F_{ab}')_2$ preparation of human IgG was prepared as described in Example 1 and $2.2 \times 10^{-7}$ mole (22 mg) cleaved in 0.015M dithiothreitol and 0.1N sodium acetate, pH 5.0 to form $F_{ab}'$ fragments which were isolated on a Sephadex G-25 column eluted with 0.1N sodium phosphate, pH 7.0 containing 1 mM EDTA. The $F_{ab}'$ fragments were then mixed with the derivatized collagenase, concentrated to about 4 ml, and allowed to react with stirring at 4° C. for 24 hours. The solution was then dialyzed in 1 liter of TBS overnight after which CaCl₂ was added to 0.01N final concentration followed by addition of β-mercaptoethylamine to a final concentration of $5 \times 10^{-4}$M (blocking of unreacted maleimide functions). This reaction proceeded at room temperature for two hours at which point the solution was applied to a Sephacryl S-200 column and eluted with TBS containing 1 mN CaCl₂ and 1 mN ZnCl₂. The conjugate containing fractions were collected, concentrated to 2.4 ml, and stored at 4° C. From the Sephacryl S-200 column absorbance profile at 280 mn the conjugate was estimated to contain about 1.5 $F_{ab}'$ per collagenase.

2. Preparation of Collagenase Solid Substrate -Collagen/Blue Dextran Beads.

Collagen beads containing blue dextran for colorant were prepared by procedures similar to those used in preparing albumin beads (T.K. Lee, T.D. Sokoloski, and G.P. Royer, *SCIENCE*, 213, 233-235 (1981)). Beads were prepared in which the high molecular weight blue dextran composed 5%, 10%, 15%, 20%, 25% and 50% of combined weight of collagen and blue dextran. In all preparations, the total combined weight of the two polymers was 3.75 g. This was added to 21.25 g water and heated to first 70° C. and then 90° C. to clarify the solution. 250 ml of corn oil in a 500 ml flask was heated to 45° C. in a water bath, and stirred rapidly with an overhead mechanical stirrer. To the stirring oil was added 7.5 ml of Span 85 followed by slow addition of the collagen solution. Bead formation occurred immediately. 600 μl of 25% glutaraldehyde was then added and stirring continued for 20 minutes. The oil was then decanted and the beads washed four times with hexane and blotted dry between pieces of paper towel. After drying, the beads were wshed three times with water and stored in water at 4° C.

3. Collagenase Conversion of Solid Substrate to Soluble Detectable Substance.

Collagenase enzymatic digestion of the blue dextran/collagen beads was examined by adding various amounts of collagenase to 0.188 g of beads with the total mixture volume brought to 3 ml by addition of TBS and 30 μl of 0.1N $CaCl_2$. The various reaction mixtures were visually examined following 1, 2, 3, 4, and 19 hours of reaction. Also, at 19 hours, absorbance values of the solutions were recorded a 615 nm to determine the maximum solution coloration due to release of blue dextran from the collagen matrix. The results of this study are summarized in Table IV for the 25% blue dextran/collagen beads. The other beam compositions provided similar results with greater or less 615 nm absorbance depending upon the amount of blue dextran in the bead compositions.

TABLE IV

| Collagenase activity* | Time to complete digestion (1, 2, 3, 4 or 19 hours) | Absorbance, supernate (615 nM) 19 hours |
|---|---|---|
| 0 | no dissolution | .167 |
| 40 ku | 2 | .808 |
| 8 ku | 3 | .791 |
| 1.6 ku | 19 | .789 |
| 320 u | 19 | .789 |

*one unit will liberate peptides from collagen equivalent in ninhydrin color to 1.0 μmole of L-leucine in 5 hours at pH 7.4 and 37° C. in the presence of calcium ions (specification from Sigma Chemical Co.)

4. Collagenase Conjugate Digestion of Substrate.

The bead digestion experiment was then repeated using the collagenase-human $F_{ab}'$ conjugate. The results are tabulated in Table V. The amounts of collagenase activity added to each tube is based upon the activity of the collagenase as received from Sigma Chemical Co. (1600 μ/mg protein) and does not reflect the effects of the conjugation procedure. Collagenase concentration was determined assuming a 1.5:1 $F_{ab}'$:collagenase ratio in the conjugate and an $\epsilon_{280}$ nm, conjugate $\sim 2.4 \times 10^5 M^{-1}$ which is the summation of the extinction coefficients of 1.5 $F_{ab}'$ and 1 collagenase at 280 nm. The reaction progress is monitored by the absorbance of 615 nM ($A_{615}$) of the supernate. The beads contained 25% blue dextran and 0.188 g beads were again used per sample.

TABLE V

| Collagenase activity in conjugate | $A_{615nm}$ | | | | | |
|---|---|---|---|---|---|---|
| | 1 hr. | 2½ hr. | 3½ hr. | 4½ hr. | 6½ hr. | 23 hr. |
| 0 | .073 | .099 | .113 | .116 | .135 | .200 |
| 8 u | .065 | .101 | .108 | .129 | .149 | .302 |
| 16 u | .075 | .127 | .153 | .179 | .217 | .637 |
| 32 u | .106 | .189 | .236 | .279 | .376 | .820 |
| 80 u | .215 | .408 | .531 | .665 | .769 | .796 |
| 160 u | .278 | .618 | .705 | .720 | .725 | .729 |
| 320 u | .347 | .783 | .782 | .785 | .791 | .791 |

The beads in the 320μ sample were completely digested by 2½ hours showing very good retention of enzyme activity in the conjugate.

5. Immunoassay Procedure Monitoring Conversion of Solid Substrate to Soluble Detectable Substance.

Immunoassay using labelled materials according to sections 1 through 4 above may be performed according to any of several formats including the competitive format described in Examples 2 and 3 and "sandwich" type assay formats. A competitive heterogeneous assay procedure for human IgG is described below. Sample containing an unknown amount of antigen is combined with collagenase-human $F_{ab}'$ and sufficient sepharose immobilized anti-human $F_{ab}'$ to bind all collagenase activity in the absence of antigen. This mixture is allowed to equilibrate as collagenase-antigen and sample antigen compete for binding to the limited amount of immobilized antibody. Supernate and solid are then separated by filtration or centrifugation. To either fraction is added collagen beads containing blue dextran. The quantity of beads need only be as much as is visually discernable, either while suspended in the sample or after settling to the bottom if the sample is opaque. If the sample totally obscures the bead presence, the beads may be visualized after decanting or filtering the liquid portion of the sample. The buffer added with the beads contains $CaCl_2$ in a final concentration near 1 mN. Digestion of the beads by any collagenase-human $F_{ab}'$ present in the fraction is allowed to proceed for several hours after which time the fraction is visually inspected to ascertain whether bead dissolution has occurred. Bead dissolution and release of blue dextran colorant in the supernate fraction indicates the presence of a sufficiently large amount of antigen in original samples, while bead dissolution and colorant release in the sepharose gel fraction indicates the opposite.

While the method of Example 3, using the labelled material of Example 1, is clearly presently the most preferred and thoroughly tested embodiment for analytical determination of analytes in samples according to the present invention, it is expected that equally effective analytical determinations may be achieved through use of other improved analytical binding assays according to the present invention.

As noted above, the present invention comprehends improved binding assays for the analytic determination of analytes in a sample by means of an association reaction of the analyte with an added laballed material or by means of competitive association reaction of the analyte and an added labelled material with an added binder for the analyte and labelled material wherein the improvement comprises employing as part of the labelled material a labelled portion which either catalyzes the formation of a detectable substance from a substrate provided in an aqueous first phase or from a substrate comprising a first phase distinct from an aqueous phase or, upon enzymatic treatment in an aqueous first phase disassociates from the labelled material to form a detectable substance; the substance so formed is capable of existing in or as a second phase distinct from the first phase. The associated and/or unassociated labelled material (dependent on the label portion employed which also determines whether a separation step is required) is contacted with the substrate or enzyme in the aqueous phase under conditions allowing formation of the substance. Also dependent on the label portion employed, the formation of substance is determined directly by determining the existence of the substance as the second distinct phase, or the first phase is brought into contact with the second distinct phase under conditions allowing transfer of detectable quantities of the ubstance from the first phase to the second phase. The transfer of the substance in the second phase is then determined directly by determining the presence of the substance in the second phase or indirectly by monitoring the decrease in amount of substrate by well-known means including colorometric, visual, or olfactory means or by instrument measurement. If desired, the amount of analyte present in the sample may also be determined by extrapolation from a standard curve constructed by preparing samples containing known amounts of analyte, performing analytical determinations according to the present invention on each known sample and plotting the results for each known sample according to well-known procedures.

The improved binding assay procedures of Examples 1, 4 and 5 illustrate the basic concept of preparation of labelled materials and Examples 2 and 3 illustrate utilizing a labelled material in a binding assay procedure wherein the presence of analyte in a sample phase is determined by detecting the presence of a substance existing in a distinct second phase and wherein the substance results from an enzymatic reaction involving the label portion of the labelled material in a first phase. More specifically, Examples 2 and 3 illustrate assays wherein determination of the presence of analytes in samples is achieved by competition between the analyte and labelled material for association with an added binder, separating associated and unassociated labelled material from each other, disposing the separated associated labelled material in an aqueous first phase comprising a buffer solution or utilizing the aqueous supernate containing unbound labelled material as the aqueous first phase, and providing a substrate in the first phase which is enzymatically converted by bound or unbound labelled material therein into a substance which is transferred in detectable amounts to and detected in a second distinct organic liquid phase brought into contact with the first phase. Due to the competition of analyte and labelled material for the added binder, it is apparent that the amount of labelled material not associated with the binder will increase with increasing amount of analyte present in the sample, and the amount of labelled material associated with binder will decrease with increasing amount of analyte present. The labelled material utilized was alkaline phosphatase conjugates of the analyte to be determined, although numerous other enzymatic labels catalyzing given substrates into known substances may be utilized such as the peroxidase and collagenase conjugates disclosed in Examples 4 and 5. Other forms of added binder may also be used including antibodies immobilized to other known support materials such as beads or the walls of the reaction vessel.

The second phase is chosen so as to be distinct from the first phase in which the substrate is provided in or exists as, and, where the substance does not itself comprise the second phase, to allow transfer of detectable quantities of detectable substances across the phase boundary to the second phase. In the foregoing examples aqueous samples (blood serum or buffer) were utilized. Possible second distinct phases, wherein the term phase is defined or homogeneous, mechanically separable portion of a physical system (Encyclo. Brit. Vol. 14 p. 204) would therefore include: gaseous phase, solid phase or liquid phases not miscible with the sample phase. The latter distinct phase in the form of an organic solvent (toluene) was selected for the illustrative Examples 2 and 3 outlined above. The second phase is also chosen based on the nature of the substance so that the substance "prefers" existence in the second phase due to solubility, gaseous nature or other physical chemical properties. The organic solvent second phase of the illustrative examples was also selected because the enzymatically produced substance p-phenylazophenol is hydrophobic and migrates across the boundary between the liquid phases and exists in detectable quantities in the non-aqueous organic liquid phase.

Other contemplated embodiments of the invention include improved assays wherein gaseous substances are monitored in the gaseous phase above liquid samples. Numerous potential labels are available which, upon enzymatic treatment, could produce substances existing in the second distinct gaseous phase. As set forth in Example 4, it has been discovered that methyoxobutanal is converted into butanedione by the enzyme peroxidase in the presence of air. Butanedione is a strongly odoriferous substance having the odor of butter and is utilized in the food industry. Enzymatic conversion of a methyoxobutanal by a peroxidase-conjugated labelled material in a nongaseous first phase into butanedione could be employed in a "smell" assay wherein detection of the butanedione is performed by sampling the air above the assay tube. References indicate that very small concentrations ($2.5 \times 10^{-5}$M butanedione) in a liquid phase result in detectable amounts in the overlying vapor phase. The presence of butanedione in the gaseous phase might also be detected by phosphorescense of the butanedione or by formation of colored products from its reaction with other compounds provided in contact with the gaseous phase including quanidine containing compounds (e.g., arginine). Similarly, solid substances insoluble in an aqueous phase may result from enzymatically catalyzed reactions utilizing substrates soluble in an aqueous phase and their existence in the solid phase used as an indication of presence of analyte. Conversely, a solid substrate for the labelled material insoluble in the aqueous phase may be enzymatically converted therein into a soluble, liquid or gaseous substance or such substances may be released from the solid substrate upon solubilization. Examples of labelled materials catalyzing formation and release of such substances are set forth in Example 5 wherein visibly discernible solid collagen/blue dextran beads insoluble in the aqueous phase are shown to be digested by collagenase into soluble substances and the blue dextran released into the aqueous phase. Choice of other substances which are capable of existing in phases distinct from a first phase are also within the scope of the present invention.

Although the illustrative examples describe an improved heterogeneous immunoassay requiring a separation of bound from unbound labelled material prior to enzymatic formation or release of the substance, it is expected that homogeneous binding assays may also be developed consistent with the invention. The labelled material employed in homogeneous assays could include label portions which are partially or totally inhibited from production of detectable substances when associated with added binder or analyte but are uninhibited when unassociated. The general concept of inhibition of enzyme activity due to binding of enzyme-labelled materials to receptors is known in the art. See. U.S. Pat. No. 4,376,825. Similarly, the labelled material employed in a homogeneous assay may include labelled portions having enzymatically clearable bonds which bonds are partially or totally inhibited from enzymatic clearage when the labelled material is bound to analyte or added binder. The general concept of utilizing such bonds is known in the art. See, U.S. Pat. No. 4,318,981.

Noncompetition association assay techniques utilizing the improvement of the present invention are also contemplated. For example, hybridization assays for DNA, RNA and other genetic material may benefit by utilization of the present invention wherein the probe has associated therewith a labelled portion which catalyzes the formation of, or, upon enzymatic treatment, releases a substance which exists in or as a second distinct phase. Antibodies may be similarly labelled and employed to determine the presence of viruses, exogeneous proteins and microorganisms in products.

The detection of the substances in distinct phases provided according to improved binding assays of the present invention make the assays well-suited for binary or "yes/no" tests employed in human health care. Since substances according to the invention exist in the second distinct phase and may be chosen to be detectable without expensive equipment such as by colormetric or olfactory means, they could be used in physicians' offices or in home kits for simple pregnancy, urinary infection, diabetes or other tests. Additionally, the assays of the present invention may also be utilized in clinical settings employing instruments to measure the absorbance of the detectable substance which measurement may be facilitated by the existence of the detectable substance in a phase distinct from the sample phase.

Consistent with the foregoing disclosure, numerous modifications and variations in the practice of the invention are expected to occur to those skilled in the art. Consequently, only such limitations as appear in the appended claims should be placed on the invention as above described.

What is claimed is:

1. A method for determining the presence of an analyte in a sample comprising contacting a sample with a reagent adapted to form a substrate phase and a product phase with said sample, said reagent including an enzyme-substrate pair, including an enzyme and a substrate, and labeled material, capable of assuming a bound position with said analyte, said labeled material having a label moiety capable of participating in reactions related to the presence of said analyte which reactions require said substrate present in said substrate phase and produce a reaction product, said label moiety is a member of said enzyme-substrate pair, said enzyme catalyzing a reaction with said substrate which produces said reaction product, said enzyme-substrate pair is selected from the group of enzyme-substrate pairs consisting of alkaline phosphatase and the substrate p-phenylazophenyl phosphate, and the enzyme collagenase and the substrate collagen/blue dextran, said reaction product capable of partitioning into said product phase distinct from said substrate phase wherein said substrate phase is a solid or a liquid, and said product phase is a liquid; and monitoring said product phase for the presence of said reaction product.

2. The method of claim 1 wherein said analyte and labeled material are members of a biological binding pair.

3. The method of claim 2 wherein said biological binding pair is selected from the group of biological binding pairs consisting of antigens and antibodies, complementary polynucleotides, drugs and drug receptors, and enzyme and enzyme substrates.

4. A kit for determining the presence of an analyte in a sample comprising: reagent adapted to form a substrate phase and a product phase with said sample, said reagent including an enzyme-substrate pair, including an enzyme and a substrate, and labeled material, capable of assuming a bound position with said analyte, said labeled material having a label moiety capable of participating in reactions related to the presence of said analyte which reactions require a substrate present in said substrate phase and produce a reaction product, said label moiety is a member of said enzyme-substrate pair, said enzyme catalyzing a reaction with said substrate which produces said reaction product, said enzyme substrate pair is selected from the group of enzyme-substrate pairs consisting of the enzyme alkaline phosphatase and the substrate p-phenylazophenyl phosphate, the enzyme collagenase and the substrate collagen/blue dextran, said reaction product capable of partitioning into said product phase distinct from said substrate phase wherein said substrate phase is a solid or a liquid and said product phase is a liquid; said reaction product detectable within said product phase to indicate the presence of said analyte.

5. The kit of claim 4 wherein said analyte and labeled material are members of a biological binding pair.

6. The kit of claim 5 wherein said biological binding pair is selected from the group of biological binding pairs consisting of antigens and antibodies, complementary polynucleotides, drugs and drug receptors, and enzyme and enzyme substrates.

7. A method for determining the presence of an analyte in a sample comprising contracting a sample with a reagent adapted to form a substrate phase and a product phase with said sample, said reagent including an enzyme-substrate pair, including an enzyme and a substrate, and labeled material, capable of assuming a bound position with said analyte, said labeled materials having a label moiety capable of participating in reactions related to the presence of said analyte which reactions require said substrate present in said substrate phase and produce a reaction product, said product capable of partitioning into said product phase distinct from said substrate phase wherein said substrate phase is a solid or a liquid, and said product phase is a gas and said product is detectable by olfactory means; and monitoring said product phase for the presence of said reaction product.

8. The method of claim 7 wherein said label moiety is a member of an enzyme-substrate pair, said enzyme catalyzing a reaction with said substrate which products said product.

9. The method of claim 8 wherein said enzyme substrate pair includes the enzyme peroxidase and the substrate 2-methyl-3-oxobutanal.

10. A kit for determining the presence of an analyte in a sample comprising: reagent including labeled material capable of assuming a bound position with said analyte, said labeled material having a label moiety capable of participating in reactions related to the presence of said analyte which produce a reaction product, and said label moiety is a member of an enzyme-substrate which includes the enzyme peroxidase and the substrate 2-methyl-3-oxobutanal, said reaction product being detectable to indicate the presence of said analyte.

* * * * *

UNITED STATES PATENT AND TRADEMARK OFFICE
CERTIFICATE OF CORRECTION

PATENT NO. : 4,804,625

DATED : February 14, 1989

INVENTOR(S) : Larry E. Morrison, et al

Page 1 of 2

It is certified that error appears in the above-identified patent and that said Letters Patent is hereby corrected as shown below:

Col. 5 line 33, "grad,e" should read --grade,--
      line 31, "(Fiar" should be --(Fair--
      line 67, "syrings" should be --syringes--

Col. 6 lines 25&26, "separation" should be --separate--

Col. 7 line 1, "preparation" should be --Preparation--
      line 12, "Sepharcryl" should be --Sephacryl--
      line 26, "hydroyyze" should be --hydrolyze--

Col. 8 line 50, "N.Y." should be --N.Y.)--

Col. 9 line 7, "tuluene" should be --toluene--

Col. 9 line 51 "$2.1 \times 10^5$" should be --$6.1 \times 10^4$--
      line 51 "there" should be --therefore--

Col. 10 line 47 "natuve" should be --native--

Col. 12 line 19 "While antibodies" should be --Whole antibody--

Col. 15 line 8 "a 615 nm" should be --at 615 nm--

Col. 15 line 12 "bean" should be --bead--

Col. 16 line 58 "ubstance" should be --substance--

UNITED STATES PATENT AND TRADEMARK OFFICE
CERTIFICATE OF CORRECTION

PATENT NO. : 4,804,625

DATED : February 14, 1989

INVENTOR(S) : Larry E. Morrison, et al

It is certified that error appears in the above-identified patent and that said Letters Patent is hereby corrected as shown below:

Col. 18 line 56 "clearable" should be --cleaveable--

Col. 18 line 58 "clearage" should be --cleavage--

Col. 18 line 61 "Noncompetition" should be --Noncompetitive--

Col. 19 lines 10-11 "colormetric" should be --colorometric--

Col. 20 line 46 "products" should be --produces--

Signed and Sealed this

Tenth Day of August, 1993

*Attest:*

MICHAEL K. KIRK

*Attesting Officer*   Acting Commissioner of Patents and Trademarks